United States Patent [19]

Malmin

[11] 4,276,880
[45] Jul. 7, 1981

[54] CANNULA AND PROCESS

[76] Inventor: Oscar Malmin, 127 E. Wayne St., Akron, Ohio 44301

[21] Appl. No.: 103,935

[22] Filed: Dec. 14, 1979

Related U.S. Application Data

[63] Continuation-in-part of Ser. No. 942,370, Sep. 14, 1978, abandoned, which is a continuation-in-part of Ser. No. 789,667, Apr. 21, 1977, abandoned, which is a continuation-in-part of Ser. No. 766,013, Feb. 7, 1977, abandoned.

[51] Int. Cl.³ ............................................. A61M 5/00
[52] U.S. Cl. ...................................... 128/221; 433/80
[58] Field of Search .................. 128/221, 218 N, 240, 128/272, 276, 347; 32/40 R, 57

[56] References Cited

U.S. PATENT DOCUMENTS

| | | | |
|---|---|---|---|
| 2,862,495 | 12/1958 | Gewecke | 128/221 |
| 3,181,336 | 5/1965 | Schofield | 128/221 X |
| 3,312,220 | 4/1967 | Eisenberg | 128/221 X |
| 3,509,880 | 5/1970 | Guttman | 128/347 X |
| 3,530,492 | 9/1970 | Ferber | 128/221 |

FOREIGN PATENT DOCUMENTS

446818 7/1923 Fed. Rep. of Germany ........... 128/221

Primary Examiner—John D. Yasko
Attorney, Agent, or Firm—Reese Taylor

[57] ABSTRACT

An improved cannula for utilization with and attachment to a dental instrument capable of selectively and alternatively injecting liquid under pressure and providing a vacuum for aspirating purposes and a process for utilizing the cannula. The improved cannula has a through central bore opening into the first end of the cannula body and has a second end that is either open to said bore or closed. Opposed slots or openings are provided in the cannula body adjacent the second end of the cannula and provide communication between the exterior of the cannula and the central bore, and also means for attaching the cannula to an instrument such as described above are provided on the body thereof. A modified form of the invention has a fully closed second end and a single elongate radiused "window" opening closely adjacent the closed end.

14 Claims, 18 Drawing Figures

CANNULA AND PROCESS

RELATED APPLICATIONS

This application is a Continuation-in-Part of Applicant's earlier filed Application Ser. No. 942,370, filed Sept. 14, 1978 and now abandoned which was a Continuation-in-Part of Applicant's earlier filed Application Ser. No. 789,667 filed Apr. 21, 1977 and now abandoned which is a Continuation-in-Part of Applicant's earlier filed Application Ser. No. 766,013, filed Feb. 7, 1977 and now abandoned.

FIELD OF THE INVENTION

This invention, in general, relates to cannulas and methods for utilization in endodontic and periodontic work and, in particular, relates to a cannula capable of being used in conjunction with an instrument which has both irrigating and aspirating capabilities wherein irrigating fluids can be delivered under pressure and withdrawn without expelling liquids or debris through the apical foramen of a root canal, for example, while still thoroughly cleansing the deepest apical extent of the root canal.

PRIOR ART STATEMENT

By way of background, it is commonly accepted that once the pulpal tissues of a tooth are irreversibly damaged or infected, the only means of preventing loss of the tooth is to thoroughly debride the root canal system of the remaining pulpal tissues and to render the system as nearly sterile and clean as humanly possible before filling the root canal spaces with various types of filling materials. It should be noted that this involves both debridement and removal of the debris from the system.

Accomplishing this clinically desirable objective in actual practice is quite difficult, however, owing to the complexities of multiple small diameter root canals, interconnections between major canals, fins, crevices, irregular walls, lateral, supplemental or accessory canals and, in general, the internal anatomical anomalies of the root canal system.

Accordingly, the success of root canal therapy is normally far from assured due to these difficulties.

Mechanically preparing and cleansing a root canal system is generally accomplished by a number of different instruments such as reamers, files, rasps, broaches, etc., which are activated by various means. These instruments, however, generally are capable only of creating their own channel and, therefore, the aforementioned complexities of the root canal systems prohibit total preparation mechanically. To compensate for this difficulty, the prior art contains a number of means designed to utilize liquids to irrigate or flush the root canal system or to use chemical solutions to chemically debride the system. The most common currently used device of this type is a conventional hypodermic syringe using a conventional needle which is inserted into the root canal system, following which the liquid is flushed through the tip of the cannula into the root canal system.

A problem exists, however, in that extreme hydraulic pressures are or may be generated by exit of the liquid from the through bore of the cannula; and the danger exists, when the needle is fully inserted, of the solution being forced into the surrounding bone and soft tissues, which can cause irritation, infection and conceivable permanent damage. In order to avoid such undesirable results, the needle is commonly retracted out of the apical regions of the system. However, this leaves the most critical area; namely, the apical portion, comparatively untouched, uncleaned and, therefore, prone to failure and ultimate loss of the tooth.

Applicant is aware of attempts to avoid undue pressure of the type just described by utilizing a hypodermic syringe with a 23 gauge, 1¼ inch needle, with the top of the needle being blunted and notched back several millimeters from the top through removal of one-half of the cannula wall. However, this still is not totally satisfactory, since when needles of this type are inserted into the apical region near the apical foramen, the remaining portion of the cannula wall acts to guide the solution out of the apical foramen, even with the very slightly reduced pressure obtained by notching of the tip.

In an attempt to compensate for the problem in question, the prior art does disclose a closed cannula having a plurality of perforations made randomly in the wall of the cannula and used with a conventional hypodermic syringe. An example can be seen in the September/1976 Edition of the Journal of Endodontics (Volume 2, page 257). This prior art discloses an attempt to reduce the pressure by allowing the solution to exit from the cannula in various directions, with little or no solution exiting into the surrounding bone or soft tissues. While this structure may be effective for that purpose, it is unable to provide means for removing the debris remaining in the canal system and provides only minimal irrigation in the critical apical one-third of the root canal system. Also, the only way to remove the debris with this type of cannula is through a process of flushing, which is of questionable success in the maxillary teeth and markedly unsuccessful in the mandibular teeth. Accordingly, since root canal systems present "blind-end" cavities, employment of vacuum or suction for the purpose of retrieving the solution as well as the debris is not only necessary but the only presently existing practical approach.

In order to overcome these difficulties, the prior art has disclosed various means which permit both irrigating and aspirating actions to be performed. Applicant has a number of U.S. patent, such as U.S. Pat. Nos. 3,745,655; 3,807,048; 3,816,921; and 3,049,748 of this type. Kahn U.S. Pat. No. 3,871,099 also employs the principle of alternately irrigating and aspirating through the same cannula using selective valving systems permitting reduced, controlled injection pressures and fluid amounts. While devices such as illustrated in these patents are satisfactory, in general, there still are some limitations on use of the same when a conventional cannula is employed; and it is the purpose of this invention to disclose an improved cannula for use with such instruments in order to maximize their effectiveness.

Applicant is also aware of other needle-like devices in the patent prior art.

For example, Noonan U.S. Pat. No. 3,109,426 discloses a combined aspirator and irrigating instrument which is rigid and capable of performing both functions. This is accomplished, however, by means of concentric tubes one of which is intended to provide for irrigation and the other aspiration. Such an instrument may be suitable for surgical use, but in root canal work given the fact that the internal diameter of the majority of root canals does not exceed 0.30 mm. and the fact that the finest tubing currently available for 30 gauge hypodermic needles has an outside diameter of 0.30 mm., such a device would obviously not be suitable.

Meyer U.S. Pat. No. 3,085,575 also discloses a device possessing the necessary rigidity and the capability of providing for both irrigation and suction. Again, however, the double tube concept renders it impractical for root canal work although it might well be highly suitable for surgical work.

Garcia U.S. Pat. No. 3,927,672 is also of interest in that it discloses a flexible catheter type tube which, while being perforated in its wall area, would not be suitable for being passed into the root canal of tooth due to its inherent flexibility.

Travers U.S. Pat. No. 2,243,299 is an irrigating applicator intended to be inserted into large body orifices. This structure also includes the double wall or two tube concept and would not in any way be suitable for root canal work although presumably satisfactory for its intended purpose.

Penney U.S. Pat. No. 3,965,901 discloses another flexible catheter suitable only for suctioning and not for a dual function.

Applicant is also aware of Choski U.S. Pat. No. 4,058,121 which is a needle capacle of performing injection and venting, but not through the same central bore. This device also has some external features which would make it impractical for use in the constricted area of a root canal.

Albrecht U.S. Pat. No 1,192,596 is a relatively non-analogous structure although it does disclose a perforated tube suitable for injecting a liquid. However, the large number of preforations placed along the length of the nozzle would render it impractical for utilization as an irrigating device particularly in the apical third of the root canal.

Jweck U.S. Pat. No. 2,862,495 discloses a hypodermic needle which, while having an opening in its sidewall, also has a closed end formed with a sharp point which would be unsuitable for endodontic applications.

Firber U.S. Pat. No. 3,530,492 also discloses a hypodermic needle which has a bulbous end which would be unusable in most root canals.

Gettman U.S. Pat. Nos. 3,509,880; Eisenberg 3,312,220 and Schofield 3,181,336 also disclose various configurations of needles having some form of openings in their bodies. All of these devices, however, teach various types of sharp distal ends which are unsuitable for root canal work because such points tend to engage the rough inner surfaces of the canals.

German Pat. No. 446,818 (Weyl) is similar in disclosing a hollow, pointed hypodermic needle.

It is believed that none of the prior art referred to herein will accomplish the purposes of the present invention.

Thus, it is an object of this invention to provide an improved cannula and method of using it which will provide the maximum safety and effectiveness in cleansing the deepest apical areas of root canals.

It is a further object to provide an improved cannula and method of using it for cleansing and chemically debriding sulci or periodontal pockets.

It is a further object of this invention to provide an improved cannula and method of drying and sealing the shaped and cleansed root canal.

SUMMARY OF THE INVENTION

It has been discovered that irrigating-aspirating devices of the type disclosed in the above-noted patents can have their efficiency, effectiveness and safety greatly improved by utilization of an improved cannula having its tip either partially or fully closed and having lateral walls thereof relieved by slots in various patterns at a point very close to the tip.

It has been found that by utilizing such a cannula, the difficulties inherent in the hydraulic pressure generated in the irrigating operation are greatly reduced. By the same token, however, the openings, being disposed in the critical apical area and being of sufficient size, permit the aspirating function to be performed without any difficulty of the debris obstructing the central bore of the cannula or obstructing the openings.

It has also been found that with some cannulas or needles, press-fit plugs can be forced into the through bore to achieve the objectives noted above.

It has also been found that optimum results can be obtained by providing a cannula with its tip fully closed and centrically rounded and having a single, radiused, "window-like" opening at a specified location adjacent the tip.

It has been found that using the improved cannula in a specified procedure in which the improved cannula is seated to the fullest depths of the root canal preparation, the apical foramen can be sealed off to provide greater safety against inadvertant expelling of noxious liquids and materials into the tissues surrounding the root tip, while at the same time carrying the actions of irrigating and aspirating to the fullest depths of the root canal preparation.

It has also been found that with the radiused, "window-like" opening, located at the specified position very close to the closed, rounded tip, the irrigating stream is discharged in a churning, turbulent, whirlpool-like manner that will more effectively scrub and remove dentinal debris, necrotic tissue and noxious liquids found in the depths of root canal preparations.

It has further been discovered that the aspirating action of the radiused, "window-like" opening of the improved cannula not only promotes the effective suctioning and removal of the liquids and debris suspended in the liquids, but avoids blockage of the lumen during aspiration overcoming this limitation prevailing in the prior art.

It has also been found that the improved cannula can be employed in an exemplary manner to cleanse and chemically debride the sulci or periodontal pockets surrounding the teeth.

The same cannula can be employed to safely, effectively and effeciently seal root canal preparations.

Accordingly, production of an improved cannula and method of the type above-described becomes the principal object of this invention, with other objects thereof becoming more apparent upon a reading of the following brief specification, considered and interpreted in view of the accompanying drawings.

BRIEF DESCRIPTION OF THE PREFERRED EMBODIMENTS

Figures 1, 2, 3, 4, 5, 6, 7:
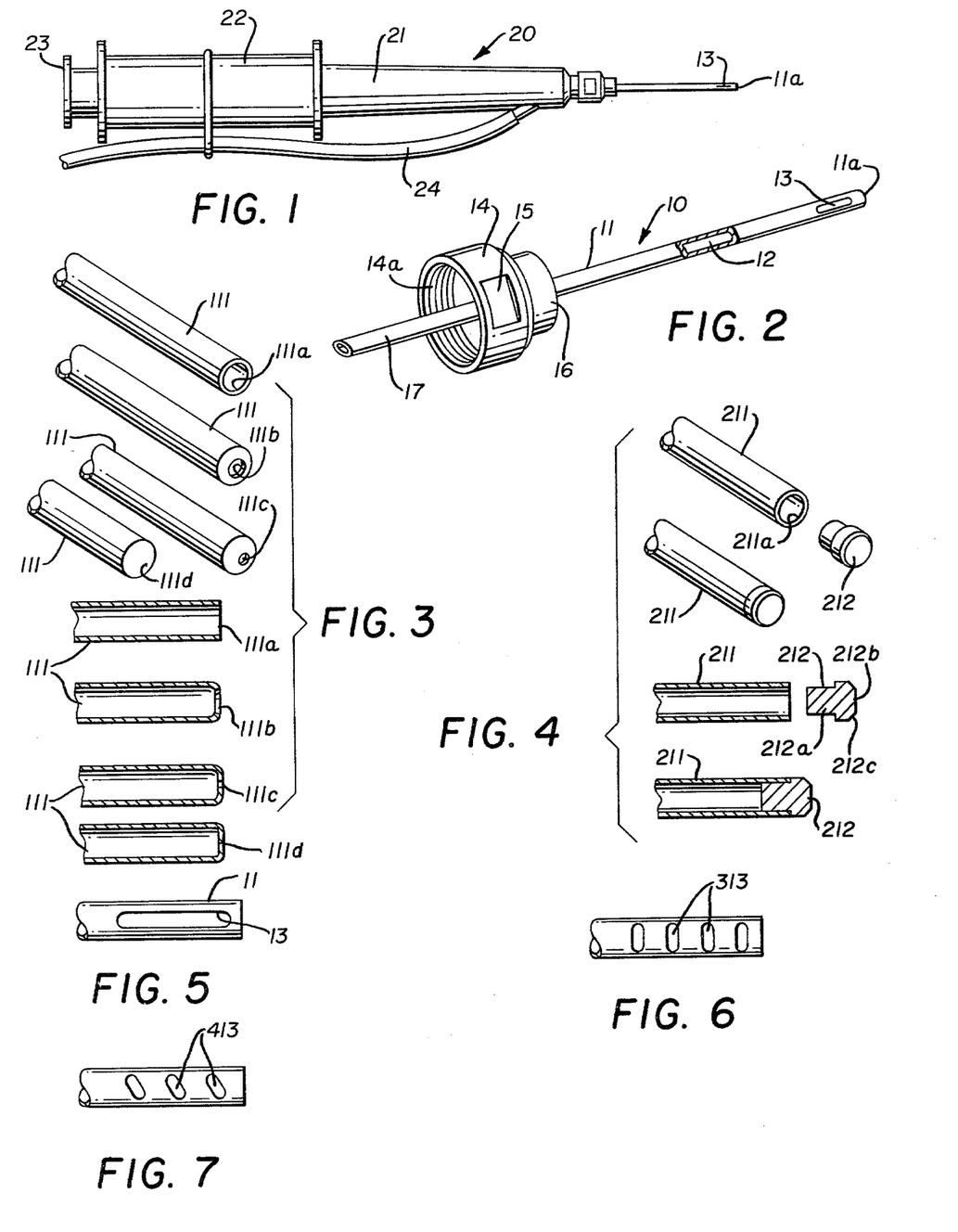
FIG. 1 is an elevational view showing one form of irrigating-aspirating instrument with the improved cannula attached thereto.
FIG. 2 is a perspective view of the improved cannula.
FIG. 3 is a partial perspective and partial sectional view of various types of cannulas.
FIG. 4 is a perspective and sectional view of a large bore cannula with the press-fit plugs employed.
FIG. 5 is a partial elevational view of the apical end of the cannula.
FIG. 6 is a partial elevational view similar to FIG. 5 showing another form of the invention.
FIG. 7 is a partial elevational view similar to FIGS. 5 and 6 showing still another form of the invention.

Referring to FIGS. 1 and 2, it will be noted that the improved cannula, generally indicated by the numeral 10, is intended to be employed with an irrigating-aspirating type syringe, generally indicated by the numeral 20 and having a body 22, coaxial barrel 21 and actuating means 23 and aspirating means 24. The particular syringe illustrated in FIG. 1 is one of the type disclosed in Malmin U.S. Pat. No. 3,949,748, and is illustrated for descriptive purposes only, with it being understood that the cannula in question has applicability for use with any irrigating-aspirating syringe.

Before describing the specific structure of the cannula 10 it should be noted that the same is intended to have a certain degree of rigidity as contrasted to a completely flexible catheter device. In the dental field, the term "cannula" has a common and accepted meaning which is that the term defines a hollow rigid member. The precise degree of rigidity is subject to some variation in accordance with standards formulated for the dental profession by American National Standards Institute. These standards set certain parameters for stiffness defined in terms of the maximum deflection permissible for appropriate gauges of material. In any event, the term cannula does have a definite meaning to those of ordinary skill in this art as does the characteristic of "rigidity."

Turning then to the specific structure of this invention, the cannula itself, generally indicated by the numeral 10, has an elongate body 11 with a through entral bore 12. This central bore opens into one end of the cannula and may or may not, as described below, open into the other end, which will be referred to herein as the "apical end" 11a. Disposed adjacent the operative end of the cannula 10 is an elongate "window" portion 13 which would normally be paired with a similar "window" in opposed relationship and which opens into the periphery and communicates with the through bore 12.

The "window" portion 13 may take any desired configuration, but should meet two basic requirements. First, the "windows" must be of sufficient size to permit the debris to be drawn into the cannula and out through tube 24 of instrument 20 without being so large as to threaten the structure integrity of the cannula. Second, the "windows" must begin as close to the apical end 11a of the cannula as possible to achieve complete aspiration of the apical area of the root canal.

Intermediate the ends of cannula 10 is a hub 14 which has internal threads 14a and which is intended to be secured to the end of the barrel 21 of the instrument 20. While threads are illustrated, other types of locking means could, of course, be employed. The hub 14 has a forward portion 16 secured to the periphery of the cannula and also has flatted areas 15 on its periphery for easy manipulation, so that the cannula can easily be grasped for attachment to or disengagement from the instrument 20.

The cannula can either be in the form of the normal medical hypodermic needle and terminate of hub 14, or have a projecting end 17 as in common with dental hypodermic needles.

Turning then to FIGS. 3 and 4, it will be noted that the working portion of the cannula 10 is disclosed in several different forms.

Referring to FIG. 3, for example, with a large diameter needle such as would be suitable for use in the coronal portion of the tooth, the apical end may be closed, as in the progression shown in FIG. 3, from the normal full opening 111a in the top illustration to the fully closed opening 111d in the bottom illustration. This closing is accomplished by swedging and may be commonly employed in cannulas used in the coronal half of the root canal system, since emission through openings 111a–111c will cause little damage.

In the event such a large diameter needle is used in the apical region of a large primary canal, such as in maxillary anterior teeth, the cannula can be swedged to closed condition as at 111d.

Also, FIG. 4 illustrates means for protecting the apical portion of the canal system when a fine gauge cannula is employed. In that instance, where a smaller diameter needle would be employed, the swedging operation is not satisfactory, since it tends to distort the needle itself. Therefore, the opening 211a in the apical end can be closed by plug 212 which has a head 212b and a body 212a and a chamgered edges 212c. This plug is simply then press fit into the opening 211a.

In both the forms of FIG. 3 and FIG. 4, the opening is closed to the desired degree; and, in both instances, there are no sharp edges or points to interfere with smooth entry and exit of the cannula into the root canal system.

While swedging and plug closure have been disclosed, it should be noted that other closure means could be used such as welding or soldering, so long as the cannula is not distorted or does not suffer a change of physical properties.

FIGS. 6 and 7 also show other possible forms for the "windows." This, FIG. 6 shows a plurality of vertically disposed openings 313,313, and FIG. 7 shows diagonally disposed openings 413,413. In both instances, it is understood that these openings would be "paired" with similar diametrically opposed openings.

Figure 8:
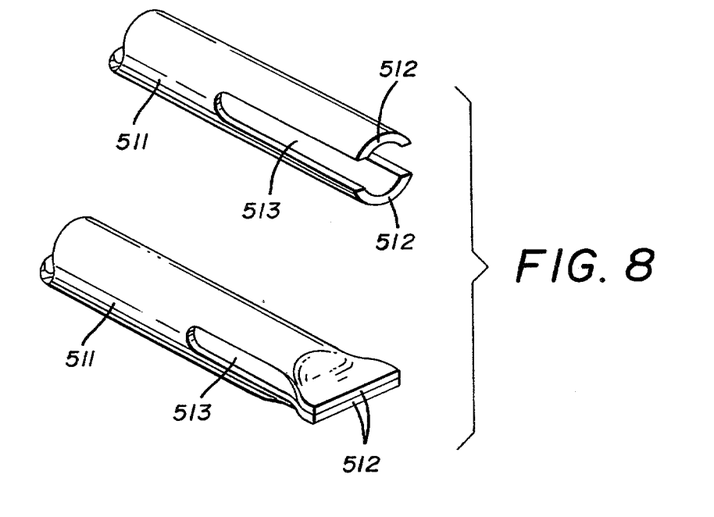
FIG. 8 is a view similar to FIG. 3 showing still another form of the invention.

FIG. 8 also illustrates another possible form of the invention. Thus, the cannula 511 is slit for some distance from its end to provide bifurcated ends 512,512 which are spaced from each other. These ends may then be pinched together and sealed by any suitable means, thus forming a closed end, indicated by the numeral 514, while retaining the windows 513.

Accordingly, then, it has been shown how an improved cannula can be employed which permits both irrigation and aspiration of a root canal system without the danger of excess hydraulic presure damaging the tissue surrounding the tooth, particularly in the apical portion thereof. Furthermore, a cannula such as described above permits the aspirating function to be performed without obstruction, with greater efficiency and effectiveness.

THE EMBODIMENT OF FIGS. 9-17

Applicant has found, through extensive experimentation and has confirmed through clinical testing, that the version of the cannula illustrated in FIGS. 9-17 is capable of producing the optimum results in practice.

In describing FIGS. 9-17, similar parts have been assigned similar numbers in the 600 series and it should also be understood that the cannula 610 of FIGS. 9-17 is intended to be utilized with a syringe such as the syringe 20 described with reference to FIGS. 1-8.

Figure 9:
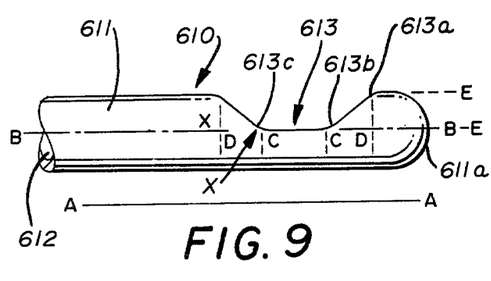
FIG. 9 is a partial side elevational view of a further modified form of the invention.
Figure 10:
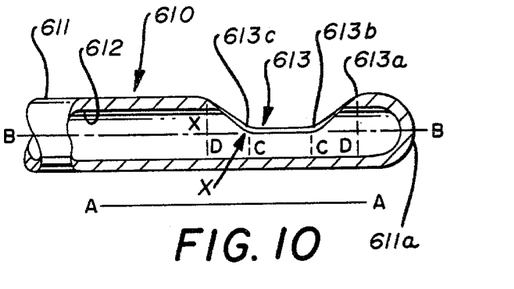
FIG. 10 is a partial sectional view taken alone line 9—9 of FIG. 9.

Referring first, then, to FIGS. 9 and 10, it will be seen that the cannula 610 has an elongate body 611 with a through central bore 612, which opens into the first end of the cannula (not shown). The body also has a fully closed operative second end 611a. Disposed closely adjacent the end 611a is a radiused elongate retangular "window-like" opening 613, which opens into the periphery of the body 611 and communicates with the central bore 612.

The opening 613 is designed to meet certain basic requirements.

First, the opening must be of sufficient size to permit the debris to be drawn into the bore 612 without blockage and removed through the tube 24 of the syringe 20. On the other hand, the opening 613 cannot be so large as to threaten the structural integrity of the body 611. Furthermore, this opening must be quite close to the tip 611a in order to achieve complete irrigation and aspiration of the full apical depths of the root canal and particularly the last one millimeter (1 mm).

Additionally, the second end or tip 611a must be smooth, rounded and centrically aligned to permit ease of entrance and access into the fullest depths of the root canal and to seal off the apical foramen 650 (see FIG. 13) for the safety of the surrounding tissues during the irrigating and aspirating phases of the cleansing of the root canal.

Still referring to FIGS. 9 and 10, it will be noted that the "working portion" A-A is illustrated in greatly enlarged fashion. This end of the cannula 610 discloses several structural characteristics of the openings 613 and the second, closed end 611a as well as the relative locations of these two features.

End 611a is symetrically rounded smooth and the final point of closure or the ultimate point of the tip should be centrically aligned with the central axis B-B of the cannula 610.

The distance from the tip 611a to the first end 613a of the opening 613 is ideally as small as possible. It has been found that preferably this should not exceed one millimeter (1 mm) regardless of the diameter of the cannula 610. Although this distance can be varied, performance characteristics are also adversely affected if it is spaced much further from the tip, keeping in mind the fact that the goal is to fully clean the ultimate apical end of the root canal.

The opening is cut into the body of the cannula by any desired means, but preferably by using a hollow grind. This forms end walls and bottom walls to the opening. These end walls and bottom walls merge in a radiused area, such as 613b and 613c. This avoids the concentration of stress in the area X and preserves the maximum strength of the body 611 so as to avoid breaking of the cannula when the opening 613 is formed or breaking of it during insertion or removal from the root canal.

The radiused nature of the cuts also prevents the opening from having its walls engage any rough edges or obstructions on the interior walls of the root canal.

Figure 11:
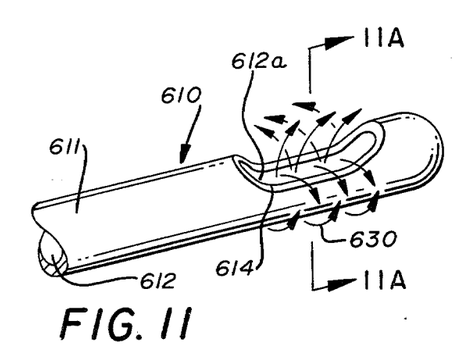
FIG. 11 is a partial perspective view of the cannula of FIG. 9 schematically showing fluid action during irrigation.
Figure 11A:
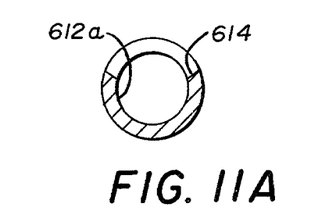
FIG. 11a is a sectional view taken on the line 11a—11a of FIG. 11.

Furthermore these radiused cuts 613b and 613c are important in the guidance of the stream of fluid emerging from the opening 613 during the irrigation step. This particular configuration creates a churning, turbulent whirlpool-like effect created by the back-pressure and the suction created by the fluid striking the walls. This churning effect is illustrated in FIG. 11 wherein the arrows 630 illustrate schematically how this fluid is passed out through the opening 613 to perform its cleaning function.

It also ought to be noted that the depth E-E of the opening 613 is approximately one-half the diameter of the body 611. In other words, approximately one-half of the wall of the body 611 is removed.

The dimensions of the opening 611 are such that in the preferred embodiment the distance D-D will range from approximately one and one-quarter millimeters (1.25 mm) in a larger diameter cannula to one millimeter (1 mm) in a smaller diameter cannula, while the dimension C-C will range from approximately one millimeter (1 mm) to three-quarters millimeter (0.75 mm), respectively. Variations are possible, but any significant variation will also significantly effect the performance characteristics.

Figure 12:
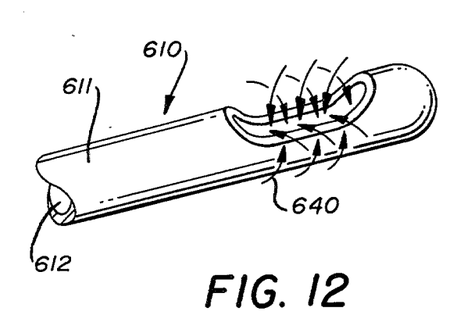
FIG. 12 is a partial perspective view of the cannula of FIG. 9 schematically showing fluid action during aspiration.

Referring again to FIGS. 11 and 11a, it will be noted that the hollow ground nature of the cut surfaces 614 of the opening 613 serves to guide the stream of irrigating liquid toward the tip 611a and, as noted above, assists in producing the churning action during the irrigating phase. This configuration also assists in effective recovery of the liquid and suspended debris during the aspirating or suctioning phase. This is illustrated in FIG. 12, by the arrows 640.

It ought to be noted that the end 611a, as mentioned above, is fully closed and rounded. This eliminates any sharp edges or points which would interfere with or prevent smooth entry into and exit from the root canal. It also is important because it permits seating of the tip 611a on top of and in a sealing relationship to the apical foramen 650 (see FIG. 13).

While the rounded tip 611a is illustrated it is possible to vary that form to a blunted centrically aligned conical form if desired, so long as it is capable of easy entrance into and exit from the root canal and sealing off the apical foramen 650.

Any desired method of forming the tip could be employed, provided there is no distortion or change in physical properties which would inhibit the performance thereof.

Figure 14:
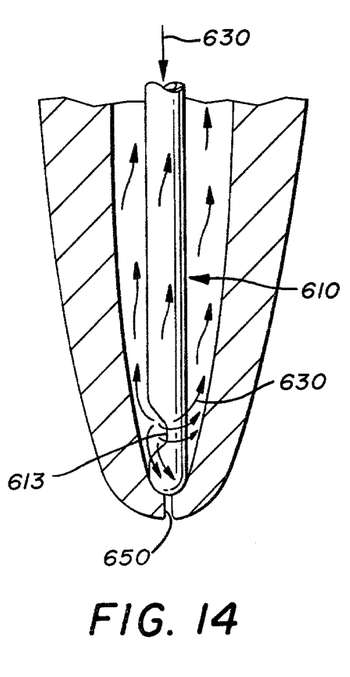
FIG. 14 is a sectional, diagrammatic view similar to FIG. 13 showing operation during the irrigation phase of endodontic therapy.

With regard to FIG. 14, which illustrates the irrigating phase, it will be noted that the material is essentially directed toward the tip 611a, but it has been found that increasing hydraulic pressure increases the effectiveness of this. In contrast, the prior art devices which employ a plurality of holes or openings along the longitudinal axis of the cannula body result in reduced pressure at the critical point which is immediately adjacent the apical end of the root canal. This is true no matter how much the hydraulic pressure is increased because these perforations or openings nearest to the source of the pressure will receive the most pressure with that pressure diminishing further away from that source.

Furthermore, the utilization of the closed tip 611a and the very short distance between the tip and the beginning of the opening 613 produces a back-pressure toward the open end of the cannula. The resultant interaction of these features produces the unique churning turbulence which provides an exceptional scrubbing and cleansing action in the fullest depths of the root canal preparation. It ought to also be noted here that it has been found that the fluid swirls around and encircles the second or apical end of the cannula, thus effecting the scrubbing and cleansing action of the root canal walls even away from the opening 613. This also results in any irregularities, such as accessory canals, "fins," recesses, "ladders" and cul-de-sacs that predominate in the apical end of the root canal system being also thoroughly cleansed.

Figure 15:
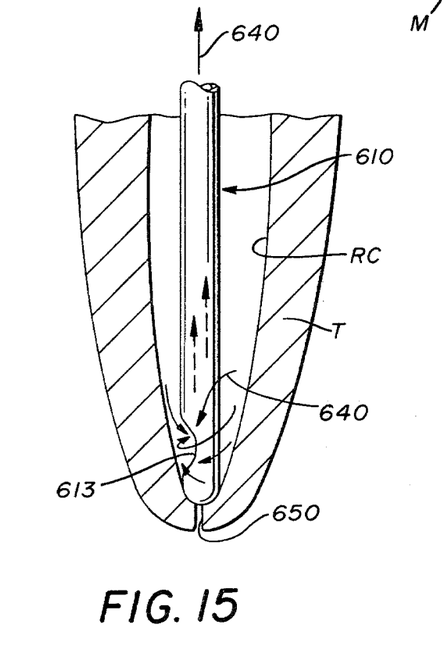
FIG. 15 is a sectional, diagrammatic view similar to FIGS. 3 and 14 showing operation during the aspiration phase of endodontic therapy.

FIG. 15 also illustrates how the aspirating or suctioning function is performed. Keeping in mind that the tip 611a is fully seated in the bottom of the root canal, closing off the apical foramen 650, the vacuum draws the liquids and suspended debris directly into the cannula through the opening 613. radiused areas 613b and 613c of the opening 613 together with the hollow ground nature of the walls 614 (see FIG. 11a) operate together to prevent blockage of the cannula during this function.

Figure 13:
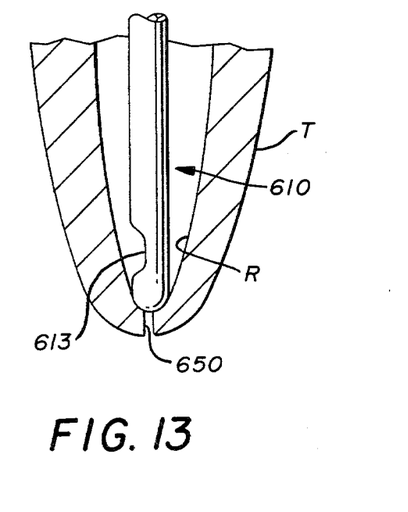
FIG. 13 is a sectional, diagrammatic view showing the cannula of FIG. 9 inserted in a root canal.

The process of utilizing the device includes fully seating the cannula 610 to the full depth of the root canal R (see FIG. 13). This seals off the apical foramen 650. With this sealed off, it is perfectly safe to inject the irrigating fluid under pressure, which is not generally possible in the prior art, due to the danger of forcing that fluid and the debris out through the apical foramen and into the surrounding tissue.

FIG. 15 illustrates, of course, the suctioning or aspirating function of the process.

Alternating these functions will ultimately provide for a satisfactorily cleaned root canal, ready for further steps in the treatment process.

Figure 16:
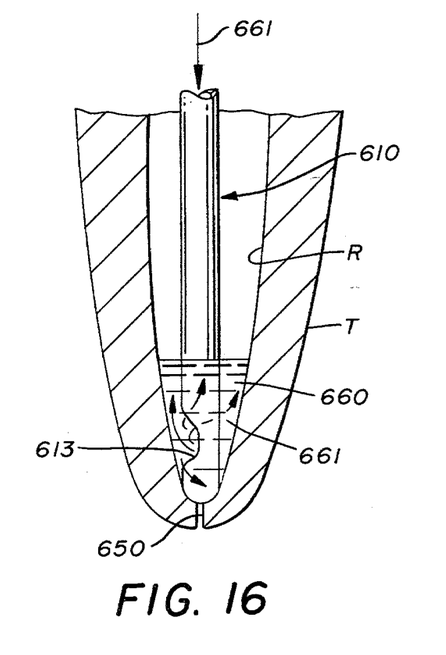
FIG. 16 is a sectional, diagrammatic view showing application of the cannula of FIG. 9 applied to the sealing of root canals.

Referring to FIG. 16, it will be seen how this same cannula can be employed in a process for sealing the root canal. It will be understood that the root canal has been properly prepared, cleaned and dried. It is then possible to inject suitable root canal filling materials 661 through the opening 613 without fear of injecting the filling materials through the apical foramen 650 and into the surrounding periapical tissues.

Once the apical third of the root canal has been filled with the sealing preparation 661, the cannula 610 can be slowly withdrawn, continuously injecting the filling material which will fill the space previously occupied by the cannula. In this manner, the entire root canal preparation can be homogeneously and thoroughly filled.

Figure 17:
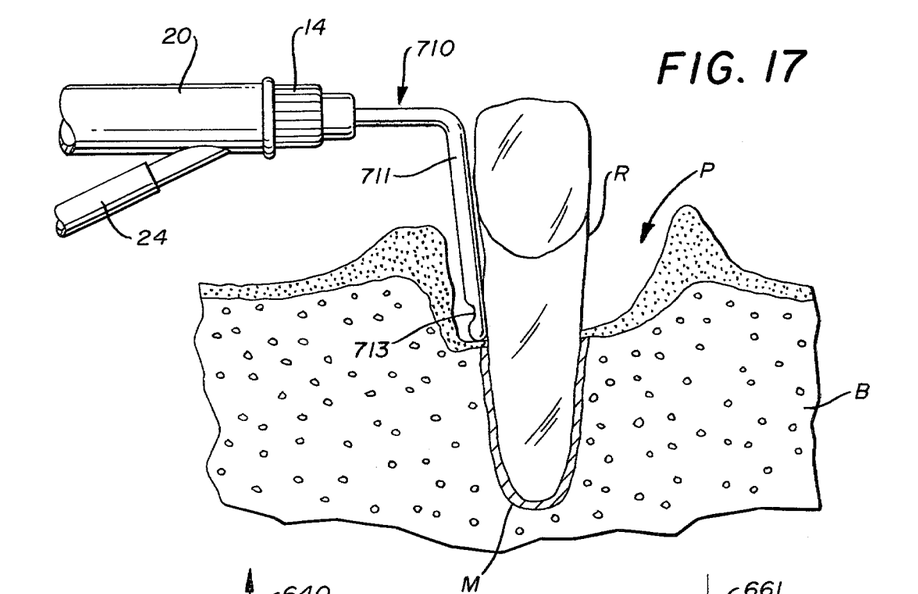
FIG. 17 is a sectional, diagrammatic view showing application of the cannula of FIG. 9 applied to the cleansing of periodontal pockets.

Referring to FIG. 17, it wil be noted that this improved cannula can also be employed to irrigate and chemically debride periodontal pockets which occur around the roots of teeth.

These pockets develop for various reasons due to bacterial plaque, calcification of bacterial plaque, noxious by-products of bacterial activity and food debris. The inability to thoroughly clean the pockets or sulcus formed between the gum tissue and the neck areas of the roots of teeth is the primary limitation of treating periodontal disease.

Research indicates that if the sulcus, which deepens into pockets in periodontal disease, can be kept clean, then the disease can be controlled or even arrested. Commonly available cleansing means, such as toothbrushes, pulsating water devices, dental floss, etc. only haphazardly clean the sulcular depths and do not reliably reverse or may not even control the progressively destructive nature of the disease.

Furthermore, as the sulcus deepens into pockets of four millimeters (4 mm) or more, the oral hygene devices are almost totally ineffective, which requires the corrective measure of periodontal surgery. This is, of course, expensive and undesirable and it is desirable to easily and routinely cleanse the sulcus or pockets.

Referring then to FIG. 17, it will be noted that the improved cannula 710, which in this form is bent at essentially right angles, can be readily employed in periodontal pockets P with utilization of the syringe 20 which has been described fully above.

The cannula 710 has a body 711 and an opening 713 as described above. The end of the body 711 can be inserted into the pocket P formed between the root R to the full depth of the pocket P which, of course, occurs because of the loss of bone B. The smooth, rounded end of the body 711 can enter into the fullest depths of the pocket without any undue obstruction or laceration of the soft tissues. Additionally, the end can actually be slid down along the surface of the root R to conveniently guide the end to the full depth of the pocket P. When the end is fully seated in the pocket, the process of irrigation and aspiration can be carried out through means of the opening 713. This will effectively, efficiently and safely treat the pocket and cleanse. In addition, chemical agents or appropriate professionally accepted compositions can be employed to chemically debride or chemically surgerize the periodontal pocket in this method.

While a full and complete description of the invention has been set forth in accordance with the dictates of the Patent Statutes, it should be understood that modifications can be resorted to without departing from the spirit hereof or the scope of the appended claims.

What is claimed is:

1. A cannula for attachment to and use with an instrument capable of selectively supplying fluid under pressure and a suction force, comprising:

(A) an elongate, cylindrical, rigid body having a central, longitudinally extending bore and having first and second ends;

(B) said central bore opening into said first end of said body;

(C) said second end of said body being closed smooth, and rounded;

(D) said body being imperforate throughout substantially its entire length;

(E) said body having only one elongate opening in its wall with one end thereof being disposed in close adjacency with said closed end; and (F) attachment means carried by said first end for releasable engagement with said instrument.

2. The cannula of claim 1 wherein said elongate opening has a depth substantially equal to one-half the diameter of said body.

3. The cannula of claim 2 wherein said elongate opening has
   (A) opposed end walls; and
   (B) opposed bottom walls;
   (C) said end walls merging into said bottom walls with the area of such merger being radiused.

4. The cannula of claim 3, where said bottom walls taper inwardly and downwardly from the peripheral wall of said body toward the interior thereof.

5. The cannula of claim 1 wherein said closed second end of said body tapers from the outer diameter of said body to a lesser diameter at its ultimate end.

6. The cannula of claim 5 wherein the lesser diameter portion of said second end is symmetrical with the center line of said body.

7. The cannula of claim 1 wherein said one end of said elongate opening is disposed approximately one millimeter (1 mm) from said second closed end of said body.

8. The cannula of claim 3, wherein said opening has a length of from approximately one millimeter (1 mm) to approximately one and one-quarter millimeter (1.25 mm) at its point of opening into the periphery of said body to from approximately three-quarter millimeter (0.75 mm) to one millimeter (1 mm) at its bottom.

9. The cannula of claim 1, wherein said closed second end is conical.

10. An endodontic treatment process using an irrigating-aspirating syringe to which is attached a rigid, elongate, cylindrical cannula having a longitudinal bore opening into the first end thereof, a smooth, rounded centrically-aligned fully closed second end and a substantially imperforate length dimension possessing, near its second end, at least one longitudinally extending opening radius cut to a depth of one-half the diameter of said member with said opening having proximal and distal radiused cut ends with said distal end of said window-like opening being located approximately one millimeter (1 mm) from the tip of said closed second end of said cannula, said process comprising the steps of:

(A) making a root canal preparation by enlarging the root canal through reaming, filing or milling thereby removing portions of pulpal tissue and dentin;

(B) inserting the second end of the cannula to the full depth of said preparation of channel thereby sealing off the apical foramen;

(C) irrigating the fullest apical depths of said preparation with liquids and chemical solutions under pressure which exit said opening in a turbulent, churning, action the thereby mechanically scrubbing said fullest apical depths while simultaneously exerting a chemical cleansing action while said second end seals said apical foramen preventing said liquids, solutions, or debris exiting freely from the depths of said preparation;

(D) aspirating said fullest apical depths of said preparation by supplying suction to said opening with said negative pressure drawing said liquids, solutions or debris directly or indirectly over the surfaces of said second end into said opening for removal from said deepest apical areas of said preparation while said second end seals said apical foramen to prevent aspirating of said periapical tissues through said apical foramen;

(E) alternating said irrigation step and said aspirating step while keeping said second end fully seated over said apical foramen; and (F) finishing said cleansing actions by drying said fullest apical depths of said preparation using the aspirating step as the final step while said second end of said cannula is fully seated over said apical foramen.

11. The process of claim 10 further characterized by the steps of injecting root canal filling materials through said opening in said cannula and withdrawing the cannula from the root canal as the canal fills from the apical end outward.

12. A periodontic treatment process using an irrigating-aspirating syringe to which is attached a rigid, elongate, cylindrical cannula having a longitudinal bore opening into the first end thereof, a smooth, rounded centrically-aligned fully closed second end and a substantially imperforate length dimension possessing near its second end at least one longitudinally extending opening radius cut to a depth of one-half the diameter of said member with said opening having proximal and distal radiused cut ends with said distal end of said window-like opening being located approximately one millimeter (1 mm) from the tip of said closed second end of said cannula, said process comprising the steps of:

(A) inserting said second end of said cannula into the sulcus to the fullest depth thereof;

(B) irrigating the sulcus by injecting liquids and chemical solutions under pressure through said opening;

(C) aspirating the sulcus by supplying suction to remove the liquids and chemical solutions and debris through said opening;

(D) repeating steps B and C until the sulcus is cleansed and debrided.

13. The cannula of claim 1 wherein a press fit plug is received within said central bore in said second end of said body.

14. The cannula of claim 1 wherein said second end of said cannula is swedged closed to seal off said central bore.

* * * * *